US00RE49759E

(19) United States
(12) Reissued Patent
Silvestri et al.

(10) Patent Number: US RE49,759 E
(45) Date of Reissued Patent: Dec. 19, 2023

(54) BLOOD PROCESSING UNIT WITH HEAT EXCHANGER CORE FOR PROVIDING MODIFIED FLOW PATH

(71) Applicant: Sorin Group Italia S.R.L., Milan (IT)

(72) Inventors: Claudio Silvestri, Quarantoli Mirandola (IT); Stefano Reggiani, Medolla (IT); Marta Balzan, Mornago (IT); Thierry Dupoux, Sceaux (FR)

(73) Assignee: Sorin Group Italia S.R.L., Milan (IT)

(21) Appl. No.: 17/068,190

(22) Filed: Oct. 12, 2020

Related U.S. Patent Documents

Reissue of:
(64) Patent No.: 10,098,994
Issued: Oct. 16, 2018
Appl. No.: 15/110,684
PCT Filed: Jan. 9, 2014
PCT No.: PCT/IT2014/000005
§ 371 (c)(1),
(2) Date: Jul. 8, 2016
PCT Pub. No.: WO2015/104725
PCT Pub. Date: Jul. 16, 2015

(51) Int. Cl.
*A61M 1/00* (2006.01)
*A61M 1/16* (2006.01)
*F28F 13/12* (2006.01)

(52) U.S. Cl.
CPC ..... *A61M 1/1698* (2013.01); *F28F 13/12* (2013.01)

(58) Field of Classification Search
CPC ... A61M 1/1629; A61M 1/1698; B01D 63/02; F28D 7/103; F28D 21/0015; F28F 13/12
See application file for complete search history.

(56) References Cited

U.S. PATENT DOCUMENTS

| | | | |
|---|---|---|---|
| 3,339,341 | A | 9/1967 | Maxwell et al. |
| 3,957,648 | A | 5/1976 | Roget et al. |
| 4,038,190 | A | 7/1977 | Baudet et al. |
| 4,225,439 | A | 9/1980 | Spranger |
| 4,229,305 | A | 10/1980 | Fecondini et al. |
| 4,597,868 | A | 7/1986 | Watanabe |
| 4,639,353 | A | 1/1987 | Takemura et al. |
| 4,707,268 | A | 11/1987 | Shah et al. |
| 4,758,341 | A | 7/1988 | Banner |
| 4,902,476 | A | 2/1990 | Gordon et al. |

(Continued)

FOREIGN PATENT DOCUMENTS

| | | | |
|---|---|---|---|
| CN | 1042082 | A | 5/1990 |
| CN | 2511309 | Y | 9/2002 |

(Continued)

OTHER PUBLICATIONS

International Search Report and Written Opinion issued in Search Report and Written Opinion issued in PCT/IT2014/000005, dated Sep. 26, 2014, 9 pages.

(Continued)

*Primary Examiner* — Beverly M Flanagan
(74) *Attorney, Agent, or Firm* — Seager, Tufte & Wickhem LLP

(57) ABSTRACT

A blood processing apparatus may include a heat exchanger and a gas exchanger. At least one of the heat exchanger and the gas exchanger may be configured to impart a radial component to blow flow through the heat exchanger and/or gas exchanger. The heat exchanger may be configured to cause blood flow to follow a spiral flow path.

29 Claims, 14 Drawing Sheets

(56) References Cited

U.S. PATENT DOCUMENTS

| | | | |
|---|---|---|---|
| 5,169,530 | A | 12/1992 | Schucker et al. |
| 5,192,439 | A | 3/1993 | Roth et al. |
| 5,192,499 | A | 3/1993 | Sakai et al. |
| 5,270,004 | A | 12/1993 | Cosentino et al. |
| 5,316,724 | A | 5/1994 | Mathewson et al. |
| 5,338,512 | A | 8/1994 | Mathewson et al. |
| 5,514,095 | A | 5/1996 | Brightbill et al. |
| 5,578,267 | A | 11/1996 | Cosentino et al. |
| 5,651,765 | A | 7/1997 | Haworth et al. |
| 5,674,452 | A | 10/1997 | Carson et al. |
| 5,733,398 | A | 3/1998 | Carson et al. |
| 5,762,868 | A | 6/1998 | Leonard |
| 5,762,869 | A | 6/1998 | White et al. |
| 5,817,278 | A | 10/1998 | Fini et al. |
| 5,817,279 | A | 10/1998 | Eilers et al. |
| 5,830,370 | A | 11/1998 | Maloney, Jr. et al. |
| RE36,774 | E | 7/2000 | Cosentino et al. |
| 6,105,664 | A | 8/2000 | Gillbrand et al. |
| 6,113,782 | A | 9/2000 | Leonard |
| 6,241,945 | B1 | 6/2001 | Owen |
| 6,454,999 | B1 | 9/2002 | Farhangia et al. |
| 6,459,937 | B1 | 10/2002 | Morgan et al. |
| 6,755,894 | B2 | 6/2004 | Bikson et al. |
| 6,960,322 | B2 | 11/2005 | Stringer et al. |
| 7,431,754 | B2 | 10/2008 | Ogihara et al. |
| 7,947,113 | B2 | 5/2011 | Ogihara et al. |
| 7,981,121 | B2 | 7/2011 | Stegfeldt et al. |
| 8,142,546 | B2 | 3/2012 | Ogihara et al. |
| 8,318,092 | B2 | 11/2012 | Reggiani et al. |
| 8,388,566 | B2 | 3/2013 | Reggiani et al. |
| 8,394,049 | B2 * | 3/2013 | Reggiani ..... A61M 1/1698 604/46 |
| 8,425,838 | B2 | 4/2013 | Mizoguchi et al. |
| 8,652,406 | B2 | 2/2014 | Reggiani et al. |
| 8,685,319 | B2 | 4/2014 | Olson et al. |
| 8,795,220 | B2 | 8/2014 | Reggiani et al. |
| 8,865,067 | B2 | 10/2014 | Olson et al. |
| 8,911,666 | B2 | 12/2014 | Mizoguchi et al. |
| 9,162,022 | B2 | 10/2015 | Reggiani et al. |
| 9,402,943 | B2 | 8/2016 | Reggiani et al. |
| 2002/0039543 | A1 | 4/2002 | Ikeda et al. |
| 2002/0049401 | A1 | 4/2002 | Ghelli et al. |
| 2003/0080047 | A1 | 5/2003 | Watkins et al. |
| 2003/0175149 | A1 | 9/2003 | Searles et al. |
| 2004/0149645 | A1 | 8/2004 | Sunohara et al. |
| 2004/0175292 | A1 | 9/2004 | Ghelli et al. |
| 2004/0251011 | A1 | 12/2004 | Kudo |
| 2005/0198801 | A1 | 9/2005 | Schmid |
| 2007/0107884 | A1 | 5/2007 | Sirkar et al. |
| 2007/0166190 | A1 | 7/2007 | Ogihara et al. |
| 2007/0231203 | A1 | 10/2007 | Mizoguchi et al. |
| 2008/0234623 | A1 | 9/2008 | Strauss et al. |
| 2010/0106072 | A1 | 4/2010 | Kashefi-Khorasani et al. |
| 2010/0269342 | A1 | 10/2010 | Carpenter et al. |
| 2010/0272606 | A1 | 10/2010 | Carpenter et al. |
| 2010/0272607 | A1 | 10/2010 | Carpenter et al. |
| 2011/0268608 | A1 | 11/2011 | Reggiani et al. |
| 2011/0268609 | A1 | 11/2011 | Reggiani et al. |
| 2012/0046594 | A1 * | 2/2012 | Reggiani ..... A61M 1/1698 604/6.09 |
| 2012/0121463 | A1 | 5/2012 | Reggiani et al. |
| 2012/0294761 | A1 | 11/2012 | Reggiani et al. |
| 2013/0142695 | A1 | 6/2013 | Reggiani et al. |
| 2013/0142696 | A1 | 6/2013 | Reggiani et al. |
| 2014/0030146 | A1 | 1/2014 | Takeuchi |
| 2014/0227133 | A1 | 8/2014 | Reggiani et al. |
| 2015/0068670 | A1 | 3/2015 | Mizoguchi et al. |
| 2017/0072123 | A1 | 3/2017 | Reggiani |

FOREIGN PATENT DOCUMENTS

| | | | |
|---|---|---|---|
| CN | 1308549 | C | 9/2005 |
| CN | 2772515 | Y | 4/2006 |
| CN | 1907508 | A | 2/2007 |
| CN | 1914474 | A | 2/2007 |
| CN | 1308549 | C | 4/2007 |
| CN | 201510571 | U | 6/2010 |
| CN | 103180032 | A | 6/2013 |
| CN | 10322019 | A | 9/2013 |
| CN | 103328019 | A | 9/2013 |
| CN | 103547298 | A | 1/2014 |
| DE | 19782098 | T1 | 11/1999 |
| DE | 102007010112 | A1 | 9/2008 |
| DE | 10201002973 | A1 | 10/2011 |
| DE | 102010027973 | A1 | 10/2011 |
| EP | 0170210 | A2 | 2/1986 |
| EP | 0170210 | B1 | 2/1986 |
| EP | 0312125 | A1 | 4/1989 |
| EP | 0170210 | B1 | 9/1991 |
| EP | 0582959 | A1 | 2/1994 |
| EP | 0895786 | A1 | 2/1999 |
| EP | 1108462 | A2 | 6/2001 |
| EP | 1180374 | A1 | 2/2002 |
| EP | 1371381 | A1 | 12/2003 |
| EP | 1618906 | B1 | 1/2006 |
| EP | 1715279 | A1 | 10/2006 |
| EP | 1741458 | A1 | 1/2007 |
| EP | 1834656 | B1 | 9/2007 |
| EP | 1618906 | B1 | 9/2008 |
| EP | 1834656 | B1 | 5/2010 |
| EP | 2420262 | B1 | 2/2012 |
| EP | 2524712 | A1 | 11/2012 |
| EP | 2537543 | A1 | 12/2012 |
| EP | 2420262 | B1 | 4/2013 |
| JP | 445526 | B | 3/1969 |
| JP | S5216681 | A | 2/1977 |
| JP | S52126681 | A | 10/1977 |
| JP | S59147603 | A | 8/1984 |
| JP | 60053156 | A | 3/1985 |
| JP | S6178407 | A | 4/1986 |
| JP | S63139562 | A | 6/1988 |
| JP | S63283709 | A | 11/1988 |
| JP | 03169329 | A | 7/1991 |
| JP | H03169329 | A | 7/1991 |
| JP | H042067 | B2 | 1/1992 |
| JP | H0439862 | B2 | 6/1992 |
| JP | H04215761 | A | 8/1992 |
| JP | H05177117 | A | 7/1993 |
| JP | H0788178 | A | 4/1995 |
| JP | H08168525 | A | 7/1996 |
| JP | H11508476 | A | 7/1999 |
| JP | 2000501954 | A | 2/2000 |
| JP | 200093510 | A | 4/2000 |
| JP | 3228518 | B2 | 11/2001 |
| JP | 2002506692 | A | 3/2002 |
| JP | 3284568 | B2 | 5/2002 |
| JP | 2002306592 | A | 10/2002 |
| JP | 2003520617 | A | 7/2003 |
| JP | 2003525736 | A | 9/2003 |
| JP | 2004216143 | A | 8/2004 |
| JP | 2006034466 | A | 2/2006 |
| JP | 2007190218 | A | 2/2007 |
| JP | 2007190218 | A | 8/2007 |
| JP | 2007244880 | A | 9/2007 |
| JP | 3992377 | B2 | 10/2007 |
| JP | 2007260151 | A | 10/2007 |
| JP | 2007328114 | A | 12/2007 |
| JP | 4455260 | B2 | 4/2010 |
| JP | 201147269 | A | 3/2011 |
| JP | 5020111 | B2 | 9/2012 |
| JP | 201363121 | A | 4/2013 |
| JP | 2015144857 | A | 8/2015 |
| WO | 9004419 | A1 | 5/1990 |
| WO | 9716213 | A2 | 5/1997 |
| WO | 9719714 | A1 | 6/1997 |
| WO | 9700636 | A1 | 9/1997 |
| WO | WO1997033636 | A1 | 9/1997 |
| WO | 9822161 | A1 | 5/1998 |
| WO | 9947189 | A1 | 9/1999 |
| WO | 9958171 | A2 | 11/1999 |
| WO | 0006357 | A1 | 2/2000 |
| WO | 0166237 | A1 | 9/2001 |
| WO | 20100124087 | A1 | 10/2010 |

(56) References Cited

FOREIGN PATENT DOCUMENTS

| | | | |
|---|---|---|---|
| WO | WO2010124087 | | 10/2010 |
| WO | 2012066439 | A1 | 5/2012 |
| WO | 2012133372 | A1 | 10/2012 |
| WO | 2015107486 | A2 | 7/2015 |
| WO | 20151047486 | A2 | 7/2015 |
| WO | 2015128886 | A1 | 9/2015 |

OTHER PUBLICATIONS

International Preliminary Report on Patentability issued in PCT/IB20141065987, dated May 26, 2017, 9 pages.
European Search Report issued in EP Application No. 10161451, dated Sep. 28, 2010, 5 pages.
European Search Report issued in EP Application No. 10173436, dated Feb. 14, 2011, 7 pages.
European Search Report issued in EP Application No. 10186550, dated Jan. 27, 2011, 7 pages.
European Search Report issued in EP Application No. 10191140, dated Nov. 30, 2011, 8 pages.
European Search Report issued in EP Application No. 12187501, dated Nov. 20, 2013, 6 pages.
European Search Report issued in EP Application No. 13161841, dated Jun. 11, 2013, 6 pages.
International Preliminary Report on Patentability issued in PCT/IT2014/000005, dated Jul. 12, 2016, 6 pages.
International Search Report and Written Opinion issued in PCT/IB2012/052424, dated Oct. 24, 2012, 17 pages.
International Search Report and Written Opinion issued in PCT/IT2014/000058, dated Dec. 8, 2014, 14 pages.
International Search Report issued in PCT/IB2011/054725, dated Feb. 9, 2012, 12 pages.
Italian Search Report issued in IT Application No. IT MO20140010, completed Sep. 23, 2014, 7 pages.
International Search Report and Written Opinion issued in PCT/IT2014/000005, dated Sep. 26, 2014, 9 pages.
International Preliminary Report on Patentability issued in PCT/IT2014/000058, dated Sep. 6, 2016, 10 pages.
International Preliminary Report on Patentabiity issued in PCT/IB20141065987, dated May 26, 2017, 9 pages.
International Search Report and Written Opinion issued in PCT/IB2014/065987, dated Jul. 6, 2015, 10 pages.
International Preliminary Report on Patentability issued in PCT/IB2015/053493, dated Nov. 23, 2017, 9 pages.
International Search Report and Written Opinion issued in PCT/IB2015/053493, dated Jan. 18, 2016, 13 pages.

* cited by examiner

BLOOD PROCESSING UNIT WITH HEAT EXCHANGER CORE FOR PROVIDING MODIFIED FLOW PATH

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a national stage application of PCT/IT2014/000005, internationally filed Jan. 9, 2014, which is herein incorporated by reference in its entirety.

TECHNICAL FIELD

The disclosure pertains generally to blood processing units used in blood perfusion systems.

BACKGROUND

Blood perfusion entails encouraging blood through the vessels of the body. For such purposes, blood perfusion systems typically entail the use of one or more pumps in an extracorporeal circuit that is interconnected with the vascular system of a patient. Cardiopulmonary bypass surgery typically requires a perfusion system that provides for the temporary cessation of the heart to create a still operating field by replacing the function of the heart and lungs. Such isolation allows for the surgical correction of vascular stenosis, valvular disorders, and congenital heart defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures oxygen-poor blood, i.e., venous blood, is gravity-drained or vacuum suctioned from a large vein entering the heart or other veins in the body (e.g., femoral) and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is filtered and then returned through an arterial line to the aorta, femoral artery, or other artery.

SUMMARY

In some embodiments, the disclosure pertains to a blood processing apparatus including a housing having a blood inlet and a blood outlet, the blood inlet extending into an interior of the housing. A heat exchanger core is arranged within the housing, the heat exchanger core including a core aperture in fluid communication with the blood inlet and configured to impart turbulence to blood passing from the blood inlet to an exterior of the heat exchanger core. Heat exchanger hollow fibers are disposed about the heat exchanger core such that a heat exchanger fluid may flow through the heat exchanger hollow fibers and blood passing from the core aperture may flow across the heat exchanger hollow fibers. A cylindrical shell extends coaxially about the heat exchanger core, the cylindrical shell including an annular shell aperture disposed near an end of the cylindrical shell opposite to an end near which the core aperture is located, the annular shell aperture configured to permit blood to pass to an exterior of the cylindrical shell. Gas exchanger hollow fibers are disposed about the cylindrical shell such that gases may flow through the gas exchange hollow fibers and blood passing from the annular shell aperture may flow across the gas exchanger hollow fibers.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

DETAILED DESCRIPTION

The disclosure pertains to a blood processing apparatus that, according to various exemplary embodiments, includes one or more of a heat exchanger and a gas exchanger (also commonly referred to as an oxygenator). In some embodiments, the term oxygenator may be used to refer to an integrated structure that combines a heat exchanger and a gas exchanger in a unitary device. In various embodiments, for example, the heat exchanger and gas exchanger are disposed in a concentric fashion with one component located inside of the other component. According to other embodiments, the heat exchanger and gas exchanger are structurally distinct structures operable coupled to each other. In some embodiments, an oxygenator may be used in an extracorporeal blood circuit. An extracorporeal blood circuit, such as may be used in a bypass procedure, may include several different elements such as a heart-lung machine, a blood reservoir, as well as an oxygenator.

Figure 1:
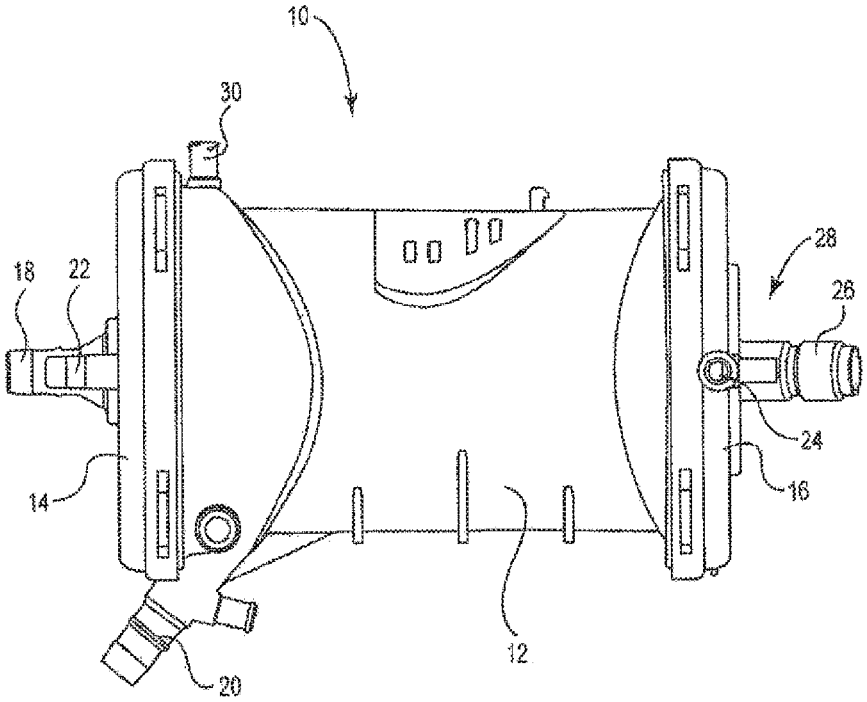
FIG. 1 is a schematic illustration of a blood processing apparatus in accordance with embodiments of the disclosure.

FIG. 1 is a schematic illustration of a blood processing apparatus or oxygenator 10. While the internal components are not visible in this illustration, the oxygenator 10 may include one or more of a heat exchanger and a gas exchanger. According to some embodiments, the heat exchanger and the gas exchanger are integrated into a single structure that forms an oxygenator housing. The oxygenator 10 includes a housing 12, a first end cap 14 that is secured to the housing 12 and a second end cap 16 that is secured to the housing 12. In some embodiments, the housing 12 may include other structure that enables attachment of the housing 12 to other devices. While the housing 12 is illustrated as largely cylindrical in shape, in some embodiments, the housing 12 may have a rectangular or other parallelogram cross-sectional shape. Each of the heat exchanger and the gas exchanger may have generally the same sectional shape or each may have a different sectional shape. In some embodiments, the heat exchanger may be inside the gas exchanger while in other embodiments the gas exchanger may be located within the heat exchanger. In some embodiments, the heat exchanger and the gas exchanger may be concentric.

In some embodiments, a blood inlet 18 extends into the housing 12 and a blood outlet 20 exits the housing 12. As noted, in some embodiments the blood processing apparatus 10 includes a gas exchanger and thus may include a gas inlet 22 and a gas outlet 24. In some embodiments, the blood processing apparatus 10 includes a heat exchanger and thus may include a heat exchanger fluid inlet 26 and a heat exchanger fluid outlet 28 that is behind (in the illustrated orientation) the heating fluid inlet 26. In some embodiments, the heat exchanger fluid inlet 26 may be disposed at one end of the housing 12 while the heat exchanger fluid outlet 28 may be disposed at an opposite end of the housing 12. In some embodiments, the blood processing apparatus 10 may include a purge port 30 that may be used for purging air bubbles from the interior of the blood processing apparatus 10.

The positions of the inlets, outlets and purge port are merely illustrative, as other arrangements and configurations are contemplated. The purge port may include a valve or a threaded cap. The purge port operates to permit gases (e.g., air bubbles) that exit the blood to be vented or aspirated and removed from the blood processing apparatus 10.

Figure 2:
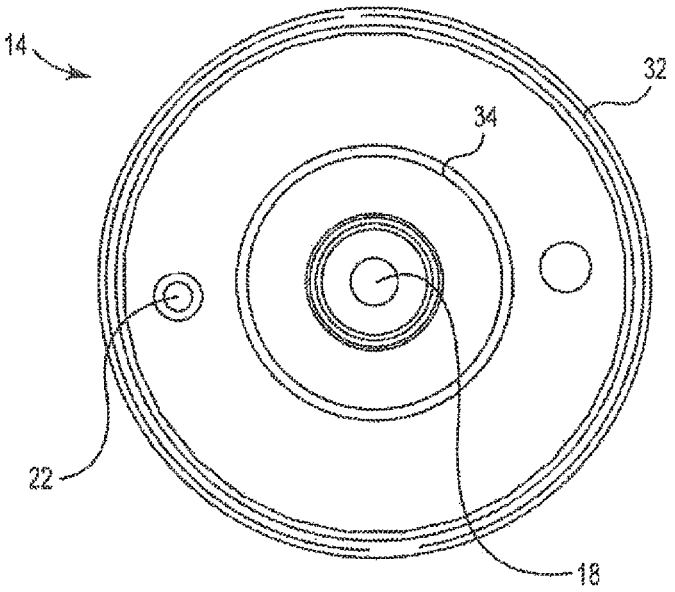
FIG. 2 is an illustration of a first end cap in accordance with embodiments of the disclosure.
Figure 3:
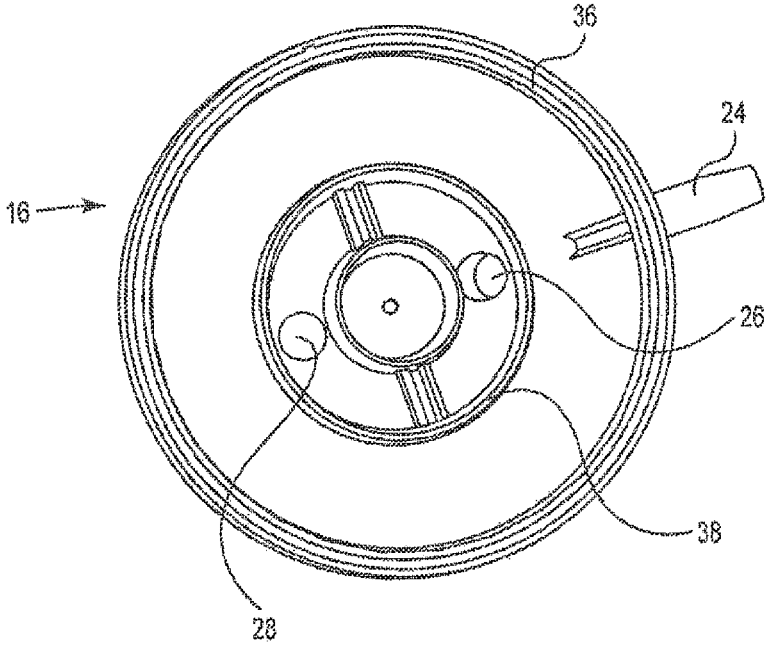
FIG. 3 is an illustration of a second end cap in accordance with embodiments of the disclosure.

FIGS. 2 and 3 illustrate the first end cap 14 and the second end cap 16, respectively. The first end cap 14 and the second end cap 16 are each configured to be secured to the housing 12. In some embodiments, the first end cap 14 and/or the second end cap 16 may be adhesively secured in place. In some embodiments, the first end cap 14 and/or the second end cap 16 may be snap-fitted into place or even threaded onto their respective ends of the housing 12.

In some embodiments, as shown in FIG. 2, the blood inlet 18 and/or the gas inlet 22 may be integrally formed with the first end cap 14. For example, in some cases the first end cap 14 may be injection molded with the blood inlet 18 and/or the gas inlet 22 formed as part of the injection molded part. In some embodiments, the first end cap 14 may be formed having apertures to which the blood inlet 18 and/or the gas inlet 22 may be attached. The first end cap 14 includes an annular ring 32 that is disposed about a periphery of the first end cap 14 and that serves, in some embodiments, as an attachment point for securing the first end cap 14 to the housing 12. In some embodiments, the first end cap 14 also includes an annular ring 34 that, as will be described subsequently, locates portions of the heat exchanger.

In some embodiments, as shown in FIG. 3, the heat exchanger fluid inlet 26 and/or the heat exchanger fluid outlet 28 may be integrally formed with the second end cap 16. For example, in some cases the second end cap 16 may be injection molded with the heat exchanger fluid inlet 26 and/or the heat exchanger fluid outlet 28 formed as part of the injection molded part. Similarly, in some embodiments, the second end cap 16 may be injected molded with the gas outlet 24 formed as part of the injection molded part. However, in some embodiments, the second end cap 16 may be formed having apertures to which one or more of the heat exchanger fluid inlet 26, the heat exchanger fluid outlet 28 and/or the gas outlet 24 may be attached. The second end cap 16 includes an annular ring 36 that is disposed about a periphery of the second end cap 16 and that serves, in some embodiments, as an attachment point for securing the second end cap 16 to the housing 12. In some embodiments, the second end cap 16 also includes an annular ring 38 that, as will be described subsequently, locates portions of the heat exchanger.

In some embodiments, one of the heat exchanger fluid inlet 26 and the heat exchanger fluid outlet 28 may be located in the first end cap 14 while the other of the heat exchanger fluid inlet 26 and the heat exchanger fluid outlet 28 may be located in the second end cap 16. In some embodiments, the heat exchanger fluid inlet 26 and outlet 28 may be located in the first end cap 14. In some embodiments, the heat exchanger fluid inlet 26 and outlet 28 may be located in the second end cap 16.

Figure 4A:
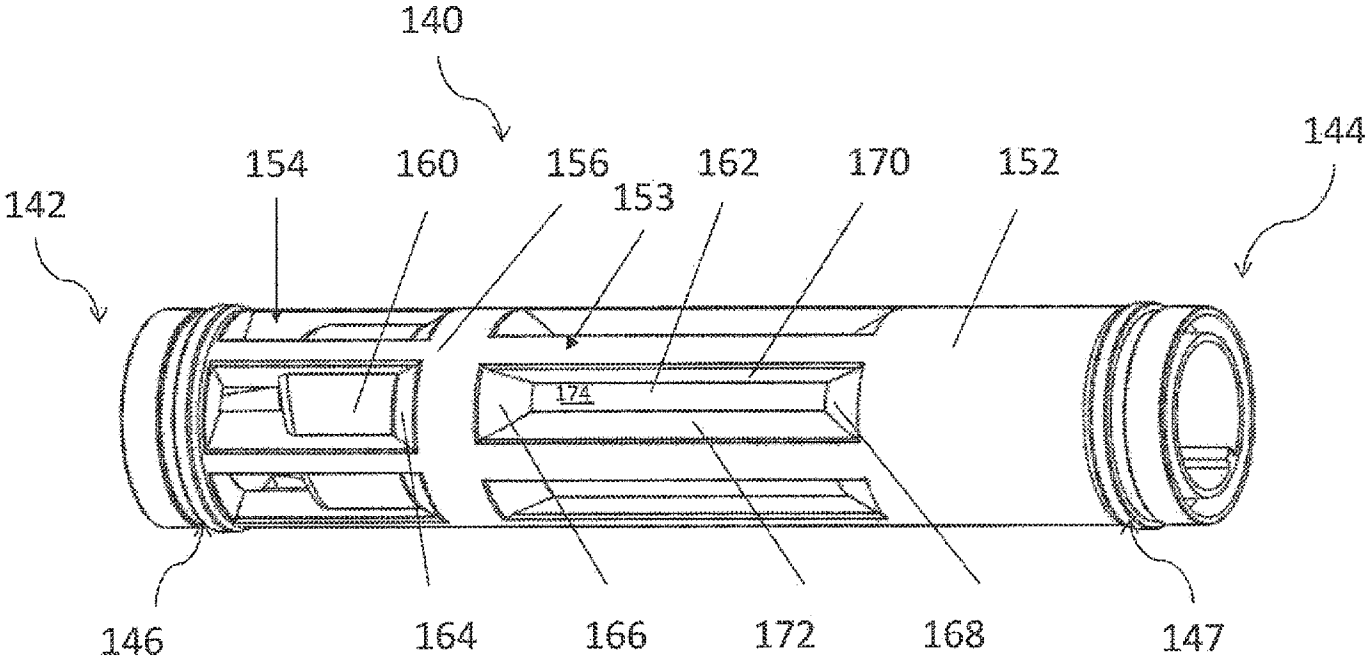
FIG. 4A is a perspective illustration of a heat exchange core in accordance with embodiments of the disclosure.

FIG. 4A is a perspective illustration of a heat exchanger core 140 having a first end 142 and a second end 144. In some embodiments, the heat exchanger core 140 may be disposed within the blood processing apparatus 10 such that the first end 142 is near the first end cap 14 while the second end 144 is near the second end cap 16. The heat exchanger core 140 includes cavities (not visible from the design) that, in some embodiments, help to locate the first end 142 relative to the first end cap 14 and similarly, the second end 144 to the second end cap 16. In some embodiments, the annular portions 146 and 147 provide a desired distance between the fiber bundle (not illustrated) and the heat exchanger 140 in order to permit a desired volume and/or depth of potting resin.

In some embodiments, the heat exchanger core 140 includes a conical deflection surface (not visible in this orientation) upon which incoming blood from the blood inlet 18 impinges. The conical deflection surface deflects the blood in a radial direction. In some embodiments, the conical deflection surface may include a divider (not shown) that assists in directing blood in particular directions. The heat exchanger core 140 includes an outer surface having one or more longitudinal ribs 153. The longitudinal ribs 153 provide mechanical support to the heat exchanger fiber bundle (not illustrated in FIG. 4A) and help to create a space between the fiber bundle and the heat exchanger core 140 in order to facilitate radial blood flow.

A core aperture 154 is formed within the outer surface 152 such that blood impinging on the conical deflection surface is deflected radially outwardly through the core aperture 154. In some embodiments, the heat exchanger core 140 may have one, two, three, four or any desired number of core apertures 154 spaced radially about the heat exchanger core 140.

In some embodiments, as illustrated, the heat exchanger core 140 includes radially disposed core ribs 152, 156. In some embodiments, the core ribs (or projections) 152, 156 deflects blood away from the outer surface of the core in a radially-outward direction. The core ribs 152, 156 are designed to impart a radial component to blood flow trajectory.

In some embodiments, the heat exchanger core 140 may also have one or more longitudinally-extending indentations 160 that are disposed ahead of the core rib 156 and one or more longitudinally-extending indentations 162 that are disposed downstream of the core rib 156. In some embodiments, a plurality of the indentations 160 and 162 are disposed circumferentially around or substantially around the outer surface 152. In some embodiments, the heat exchanger core 140 is configured to provide turbulent blood flow while providing sufficient physical support for the heat exchanger hollow fibers (not illustrated).

The indentations 160 include an angled surface 164, proximate the core rib 156, that provides a radially outward component to blood flow trajectory. The indentations 162 include a first tapered surface 166, a second tapered surface 168, a third tapered surface 170, a fourth tapered surface 172 and a bottom surface 174 that in combination assist in causing blood flow to move towards and away from the heat exchanger core 140.

Figure 4B:
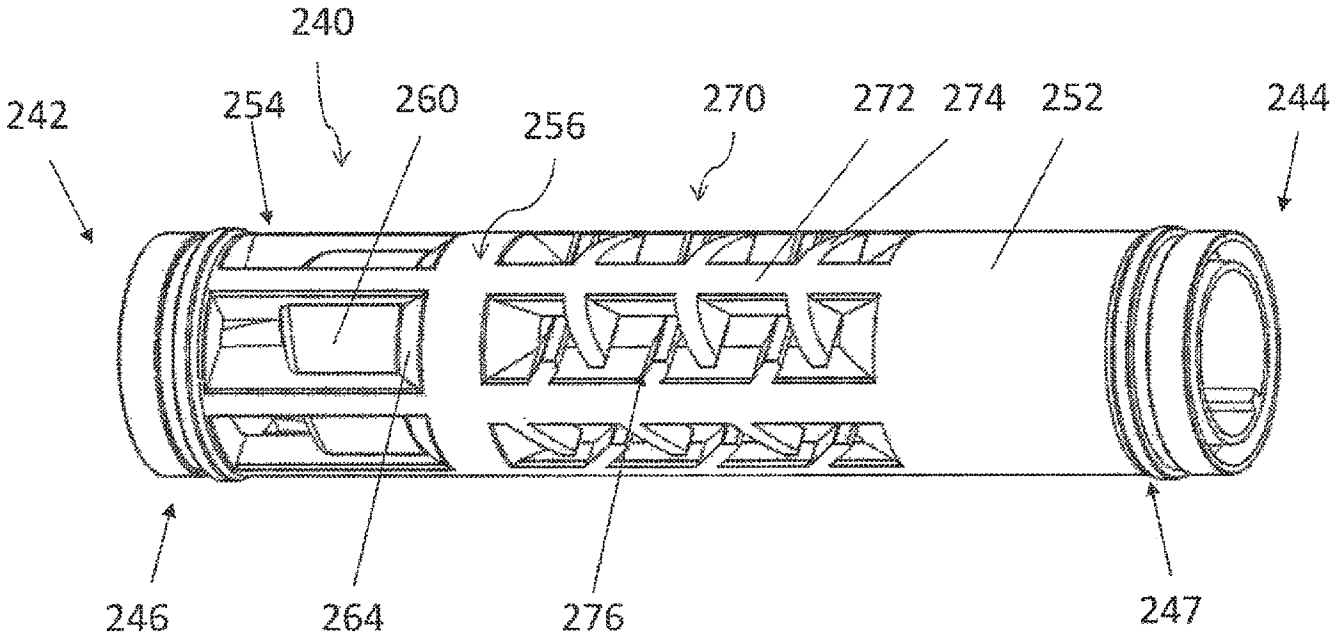
FIG. 4B is a perspective illustration of a heat exchange core in accordance with embodiments of the disclosure.

FIG. 4B is a perspective illustration of a heat exchanger core 240 having a first end 242 and a second end 244. In some embodiments, the heat exchanger core 240 may be disposed within the blood processing apparatus 10 such that the first end 242 is near the first end cap 14 while the second end 244 is near the second end cap 16. The heat exchanger core 240 includes cavities (not illustrated in the drawing) that, in some embodiments, help to locate the first end 242 relative to the first end cap 14 and Similarly, the second end 244 relative to the second end cap 16. In some embodiments, the annular portions 246 and 247 provide a desired distance between the fiber bundle (not illustrated) and the heat exchanger 240 in order to permit a desired volume and/or depth of potting resin.

In some embodiments, the heat exchanger core 240 includes a conical deflection surface (not visible in this orientation) upon which incoming blood from the blood inlet 18 impinges. The conical deflection surface deflects the blood in a radial direction. In some embodiments, the conical deflection surface may include a divider (not shown) that assists in directing blood in particular directions. The heat exchanger core 240 includes an outer surface 252. A core aperture 254 is formed within the outer surface 252 such that blood impinging on the conical deflection surface is deflected radially outwardly through the core aperture 254. In some embodiments, the heat exchanger core 240 may have one, two, three, four or any desired number of core apertures 254 spaced radially about the heat exchanger core 240.

In some embodiments, as illustrated, the heat exchanger core 240 includes a radially disposed core rib 256. In some embodiments, the core rib (or projection) 256 deflects blood away from the outer surface 252 in a radially-outward direction. The core rib 256 is designed to impart a radial component to blood flow trajectory. In some embodiments, the heat exchanger core 240 is configured to provide turbulent blood flow while providing sufficient physical support for the heat exchanger hollow fibers (not illustrated).

In some embodiments, the heat exchanger core 240 may also one or more longitudinally-extending indentations 260 that are disposed ahead of the core rib 256. In some embodiments, a plurality of the indentations 260 are disposed circumferentially around or substantially around the outer surface 252. The indentations 260 include an angled surface 264, proximate the core rib 256, that provides a radially outward component to blood flow trajectory.

In some embodiments, the heat exchanger core 240 includes a blood turbulence section 270 that is disposed downstream of the core rib 256. The blood turbulence section 270 includes several longitudinally-extending ribs 272 that are intersected by radial ribs 274. In some embodiments, the ribs 272 and the radial ribs 274 represent portions of the outer surface 252. A plurality of voids 276 are formed within the outer surface 252, in between the ribs 272 and the radial ribs 274. Blood impinging on the blood turbulence section 270 will splash off in a variety of directions, thereby improving blood flow across the heat exchanger hollow fibers (not illustrated).

Figure 4C:
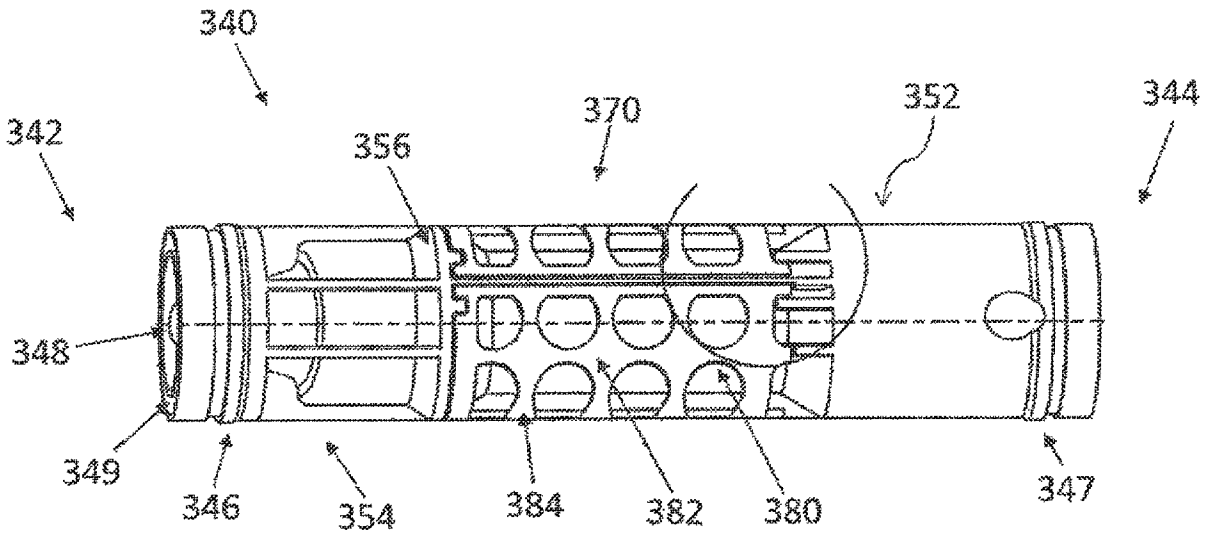
FIG. 4C is a perspective illustration of a heat exchange core in accordance with embodiments of the disclosure.

FIG. 4C is a perspective illustration of a heat exchanger core 340 having a first end 342 and a second end 344. In some embodiments, the heat exchanger core 340 may be disposed within the blood processing apparatus 10 such that the first end 342 is near the first end cap 14 while the second end 344 is near the second end cap 16. The heat exchanger core 340 includes cavities (349, while the second cavity is not presented in the drawing) that, in some embodiments, help to locate the first end 342 relative to the first end cap 14 and Similarly, the second end 344 relative to the second end cap 16. In some embodiments, the annular portions 346 and 347 provide a desired distance between the fiber bundle (not illustrated) and the heat exchanger 340 in order to permit a desired volume and/or depth of potting resin.

The heat exchanger core 340 includes a conical deflection surface 348 upon which incoming blood from the blood inlet 18 impinges. The conical deflection surface 348 deflects the blood in a radial direction. In some embodiments, the conical deflection surface 348 may include a divider (not illustrated) that assists in directing blood in particular directions. The heat exchanger core 340 includes an outer surface 352. A core aperture 354 is formed within the outer surface 352 such that blood impinging on the conical deflection surface 348 is deflected radially outwardly through the core aperture 354. In some embodiments, the heat exchanger core 340 may have one, two, three, four or any desired number of core apertures 354 spaced radially about the heat exchanger core 340. In some embodiments, the heat exchanger core 340 is configured to provide turbulent blood flow while providing sufficient physical support for the heat exchanger hollow fibers (not illustrated).

In some embodiments, the heat exchanger core 340 includes a blood turbulence section 370 that is disposed downstream of the core rib 356. The blood turbulence section 370 includes a recessed portion 380 extending into the outer surface 352 and a grid 382 that extends across the recessed portion 380. In some embodiments, the grid 382 extends at least substantially co-cylindrically with the outer surface 352. The grid 382 may be formed of any suitable metallic or polymeric material, and may be attached to the heat exchanger core 340 in any suitable manner. The grid 382 includes a plurality of apertures 384. The grid 382 provides mechanical support to the heat exchanger fiber bundle and provides a space for radial blood flow.

Figure 5A:
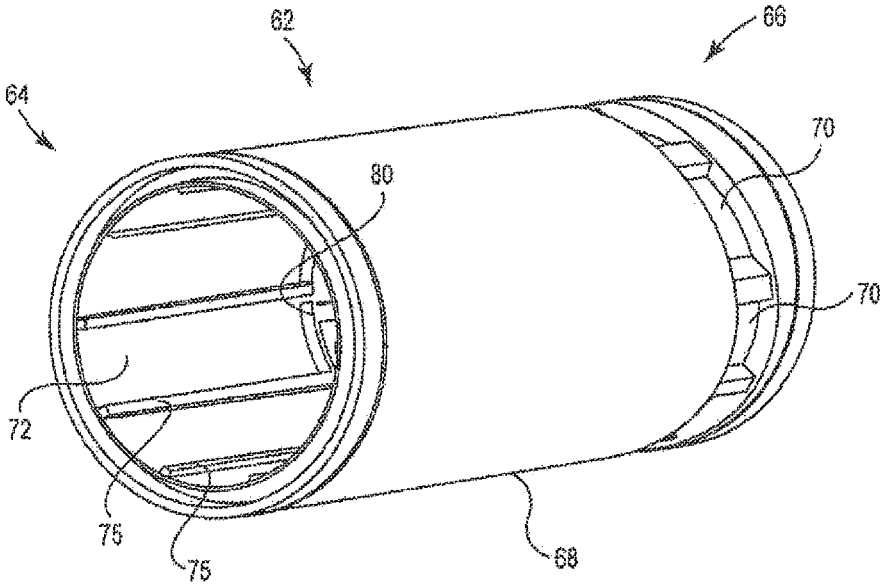
FIG. 5A is a perspective view of a cylindrical shell forming a barrier between a heat exchanger and a gas exchanger in accordance with embodiments of the disclosure.
Figure 5B:
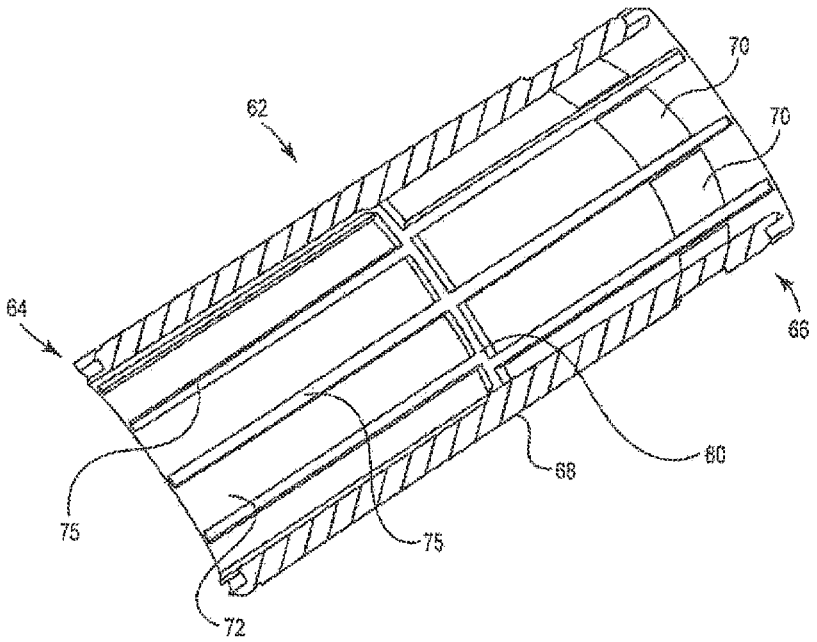
FIG. 5B is a cross-sectional view of the cylindrical shell of FIG. 5A.
Figure 6:
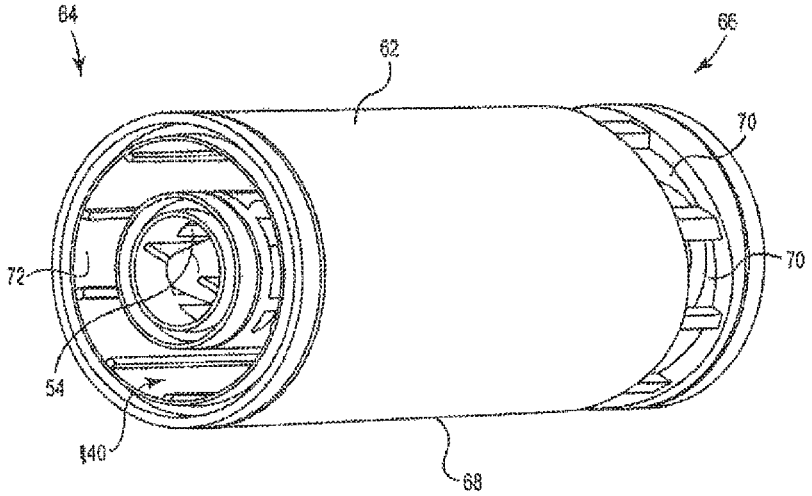
FIG. 6 is a perspective view of the heat exchanger core of FIG. 4 disposed within the cylindrical shell of FIG. 5.

FIG. 5A is a perspective illustration of a cylindrical shell 62 that may be disposed within the housing 12 and arranged coaxially with the heat exchanger core 40 (see FIG. 6). FIG.

5B is a cross-sectional view of the cylindrical shell 62. The cylindrical shell 62 includes a first end 64 and a second end 66. In some embodiments, the cylindrical shell 62 may be disposed within the housing 12 such that the first end 64 is near the first end cap 14 while the second end 66 is near the second end cap 16.

The cylindrical shell 62 includes an outer surface 68. A shell aperture 70 is formed within the outer surface 68 such that blood flowing between the outer surface 52 of the heat exchanger core 40 and an inner surface 72 of the cylindrical shell 62 can exit the cylindrical shell 62. In some embodiments, the inner surface 72 of the cylindrical shell 62 may include one or more shell ribs 80 that protrude from the inner surface 72 and extend toward the heat exchanger core 140, 240, 340. The one or more shell ribs 80 deflect blood away from the inner surface 72 in a radially inward direction. In some embodiments, the one or more shell ribs 80 may, in combination with the core ribs 56 and 58, interrupt longitudinal blood flow and impart a radial flow component to blood flow through the heat exchanger, i.e., between the outer surface 52 of the heat exchanger core 40 and the inner surface 72 of the cylindrical shell 72. In some embodiments, the heat exchanger core 140, 240, 340 may also include one or more longitudinally-extending ribs 75 that may serve to create a distance between the heat exchanger fiber bundle and the cylindrical shell 72 in order to allow a radial flow path between the heat exchanger core 140, 240, 340 and the cylindrical shell 62.

In some embodiments, the cylindrical shell 62 may have one, two, three, four, five, six or any desired number of shell apertures 70 spaced radially about the cylindrical shell 62. As illustrated in FIG. 6, the core aperture(s) 54 and the shell aperture(s) 70 are generally disposed at opposite ends of the blood processing apparatus 10. Thus, blood entering the volume between the outer surface 52 of the heat exchanger core 40 and an inner surface 72 of the cylindrical shell 62 is forced to flow at least substantially the entire length thereof before exiting the cylindrical shell 62.

Figure 7:
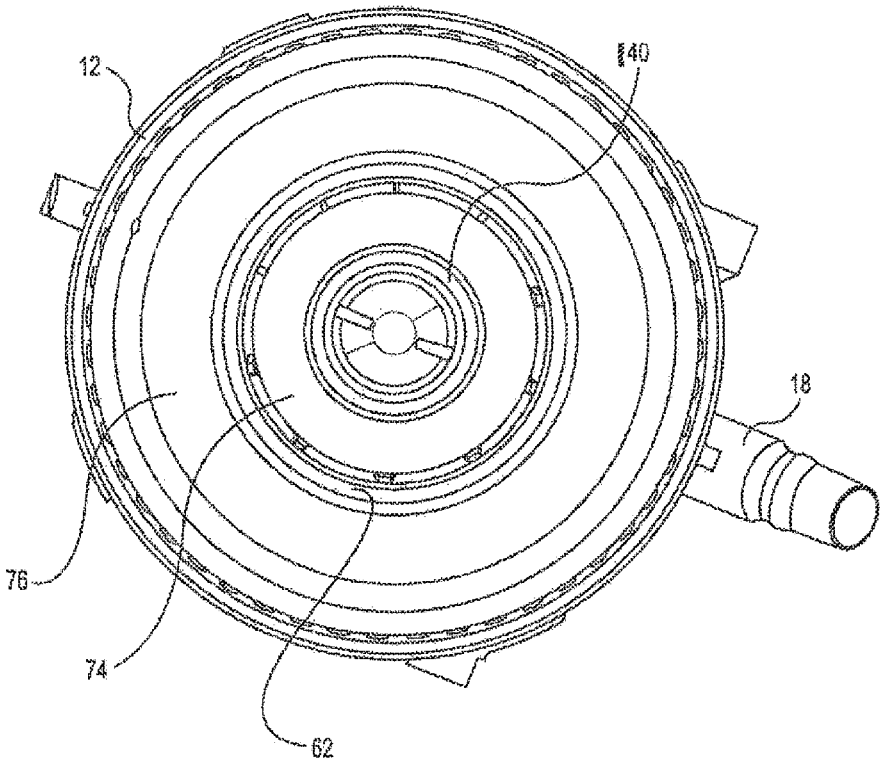
FIG. 7 is a cross-sectional view of the blood processing apparatus of FIG. 1.

FIG. 7 is a cross-sectional illustration of embodiments of the blood processing apparatus 10, illustrating the coaxial arrangement between the housing 12, the heat exchanger core 40 and the cylindrical shell 62. In some embodiments, the blood processing apparatus 10 includes a schematically illustrated heat exchanger element 74 as well as a schematically illustrated gas exchanger element 76.

In some embodiments, the heat exchanger element 74 includes a number of hollow fibers through which a heating fluid such as water can flow. The blood may flow around and past the hollow fibers and thus be suitably heated. In some embodiments, the hollow fibers may be polymeric. In some cases, metallic fibers may be used. In some embodiments, the hollow fibers may be formed of polyurethane, polyester, or any other suitable polymer or plastic material. According to various embodiments, the hollow fibers have an outer diameter of between about 0.2 and 1.0 millimeters or, more specifically, between about 0.25 and 0.5 millimeters. The hollow fibers may be woven into mats that can range, for example, from about 20 to about 200 millimeters in width. In some embodiments, the mats are arranged in a criss-cross configuration.

In some embodiments the gas exchanger element 76 may include a number of microporous hollow fibers through which a gas such as oxygen may flow. The blood may flow around and past the hollow fibers. Due to concentration gradients, oxygen may diffuse through the microporous hollow fibers into the blood while carbon dioxide may diffuse into the hollow fibers and out of the blood. In some embodiments, the hollow fibers are made of polypropylene, polyester, or any other suitable polymer or plastic material. According to various embodiments, the hollow fibers have an outer diameter of about 0.38 millimeters. According to other embodiments, the microporous hollow fibers having a diameter of between about 0.2 and 1.0 millimeters, or more specifically, between about 0.25 and 0.5 millimeters. The hollow fibers may be woven into mats that can range, for example, from about 20 to about 200 millimeters in width. In some embodiments, the mats are in a criss-cross configuration.

Figure 8:
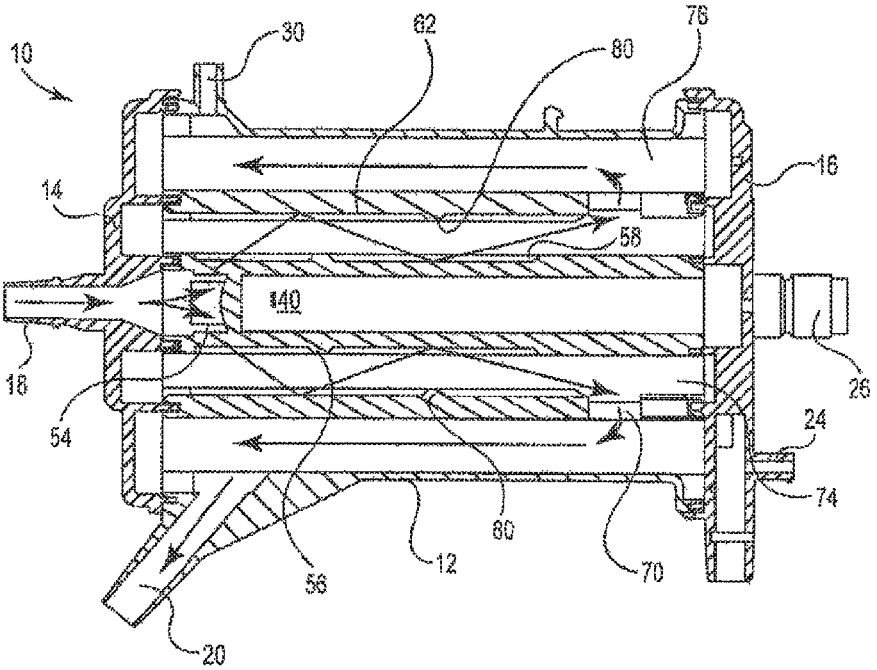
FIG. 8 is a cross-sectional illustration of a blood processing apparatus in accordance with embodiments of the disclosure.

As shown in FIG. 8, blood that enters the blood processing apparatus 10 through the blood inlet 18 is radially directed through the core aperture(s) 54 such that the blood flows over and around the hollow fibers within the heat exchanger element 74. At least some of the blood flow impinges on the inner surface 72 of the cylindrical shell 62 and is radially directed back towards the outer surface 52 of the heat exchanger core 140, 240, 340 (core 140 is illustrated). At least some of the blood flow is then directed radially outwards by the core ribs 56 and 58. The blood continues traveling back and forth radially until it reaches the shell aperture(s) 70 and enters a space between the cylindrical shell 62 and the housing 12. In some embodiments, improved heat transfer may be achieved by combining radial and longitudinal flow through the heat exchanger element 74. The blood exiting the shell aperture(s) 70 flows over and around the gas exchanger element 76 and eventually exits the blood processing apparatus 10 through the blood outlet 20.

FIG. 8 is a cross-sectional view of the blood processing apparatus 10, illustrating the relative orientation of the elements previously discussed. As shown, the heat exchanger core is centrally located, with the heat exchanger element 74 coaxially disposed about the heat exchanger core 140, 240, 340 (core 140 is illustrated). The cylindrical shell 62 is coaxially disposed about the heat exchanger element 74, followed sequentially by the gas exchanger element 76 and the housing 12. In some embodiments, the heat exchanger core 140, 240, 340 (core 140 is illustrated) may have core ribs 56 and 58 that are configured to impart a radial component to blood flow trajectory across the heat exchanger element 74. In some embodiments, the cylindrical shell 62 may have one or more radially disposed shell ribs 80 that are configured to impart a radial component to blood flow trajectory across the heat exchanger element 74.

Figure 9:
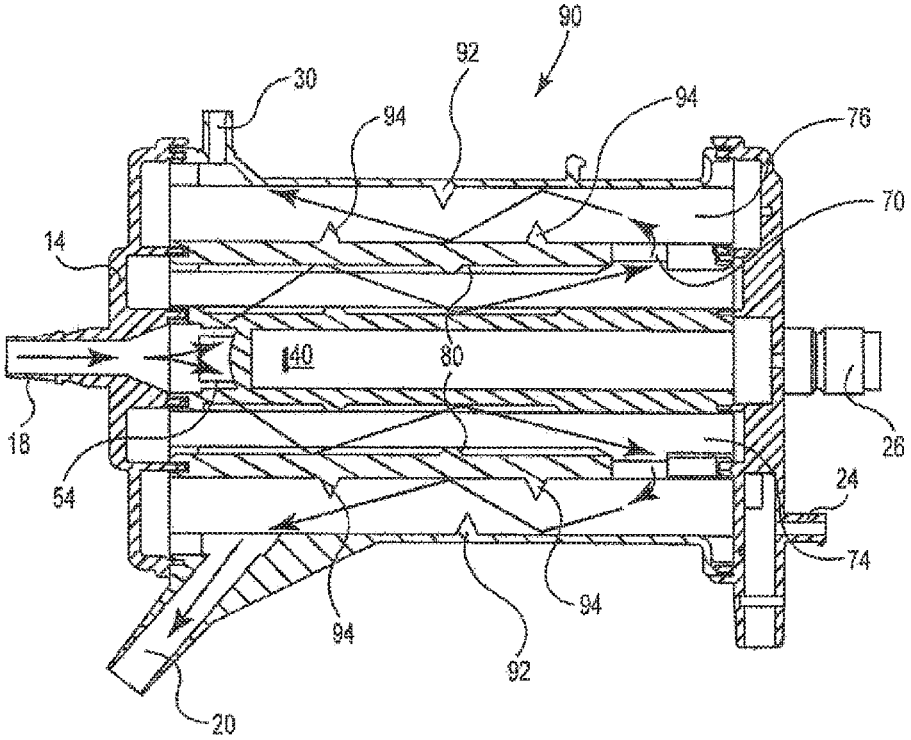
FIG. 9 is a cross-sectional illustration of a blood processing apparatus in accordance with embodiments of the disclosure.

FIG. 9 is a cross-sectional view of a blood processing apparatus 90 in accordance with embodiments of the disclosure. The blood processing apparatus 90 is similar to the blood processing apparatus 10, but includes a modified gas exchanger portion. In some embodiments, an inner surface of the housing 12 includes one or more housing ribs 92 that are configured to impart a radial component to blood flow trajectory through and across the gas exchanger element 76. In some embodiments, an outer surface of the cylindrical shell 62 includes one or more outer shell ribs 94 that are configured to impart a radial component to blood flow trajectory through and across the gas exchanger element 76. In some embodiments, improved gas transfer may be achieved by combining radial and longitudinal flow through the gas exchanger element 76.

In some embodiments, the ribs such as the core ribs 56 and 58, the shell ribs 80 and/or the housing ribs 92 may extend about 10 to about 70 percent of the distance between a surface from which they extend to an opposing surface. In some embodiments, the ribs may extend about 25 to about 50 percent of the aforementioned distance. To illustrate, the core ribs 56 and 58 may extend about 10 to about 70 percent, or about 25 to about 50 percent, of a distance between the heat exchanger core 40 and the cylindrical shell 62. In some embodiments, the ribs may form an angle with the surface from which they extend that is in the range of about 30 to about 90 degrees. In some embodiments, the ribs may form an angle of about 45 to about 60 degrees. In some embodiments, the ribs may have a height that is in the range of about 0.2 millimeters to about 3 millimeters and a width that is in the range of about 0.5 millimeters to about 10 millimeters.

Figure 10:
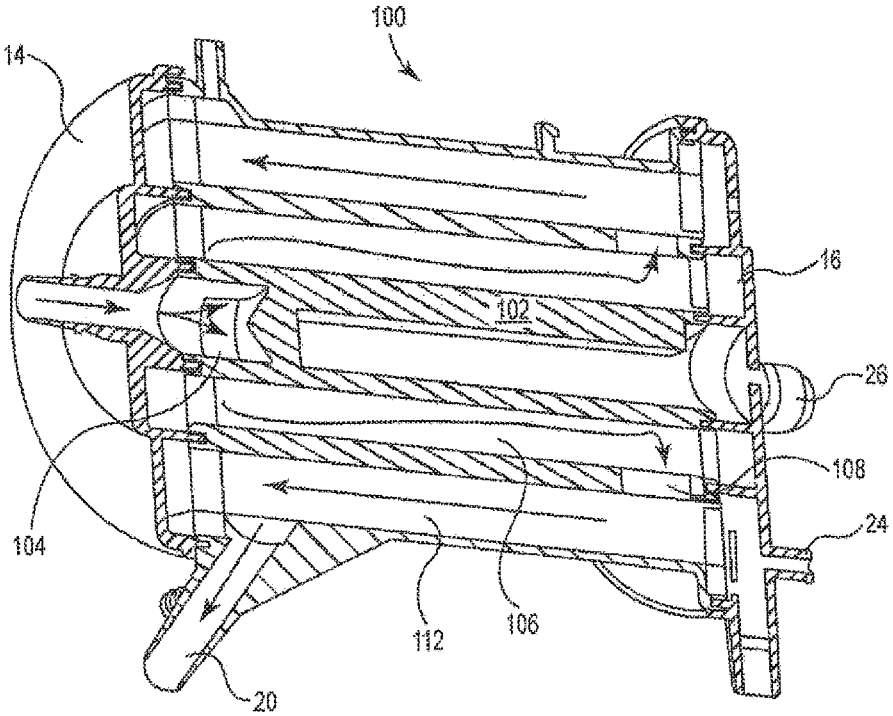
FIG. 10 is a cross-sectional illustration of a blood processing apparatus in accordance with embodiments of the disclosure.

FIG. 10 is a cross-sectional view of a blood processing apparatus 100 in accordance with embodiments of the disclosure. The blood processing apparatus 100 is similar to those discussed above, but blood flow through the heat exchanger has a spiral component. The blood processing apparatus 100 has a heat exchanger core 102 that includes one or more core apertures 104. Blood passes through the one or more core apertures 104 and enters a heat exchanger element 106 that as discussed above may include a number of hollow fibers. Blood exits the heat exchanger element 106 through one or more shell apertures 108 and then passes longitudinally through a gas exchanger element 112 before exiting through the blood outlet 20.

Figure 11:
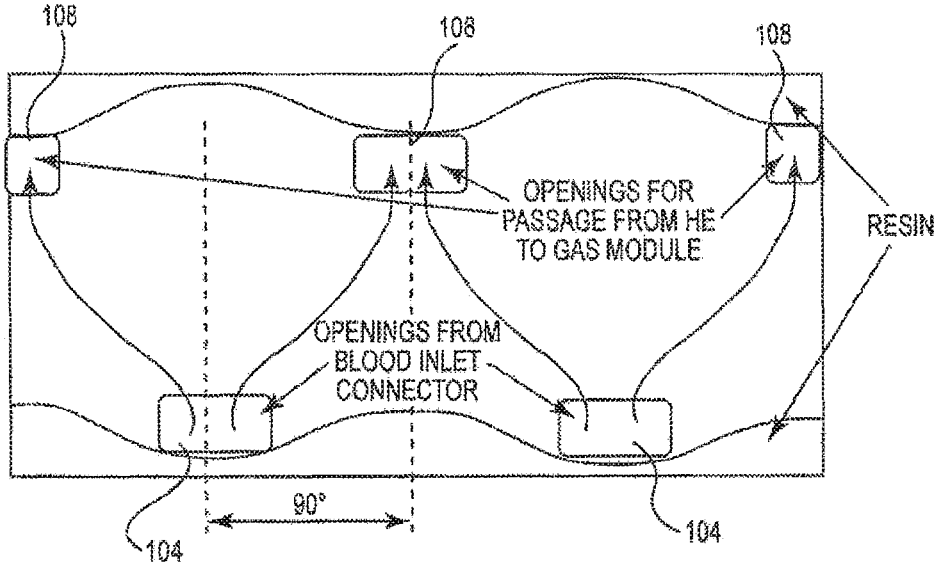
FIG. 11 is a diagram illustrating blood flow paths in the blood processing apparatus of FIG. 10.

As shown in FIG. 10 that the core apertures 104 and the shell apertures 108 are longitudinally spaced apart such that blood entering the heat exchanger element 106 passes the length of the heat exchanger element 106 before exiting into the gas exchanger element 112. The core apertures 104 and the shell apertures 108 are radially spaced apart from one another. As schematically shown in FIG. 11, for example, the core apertures 104 may be spaced about 180 degrees apart from each other. The shell apertures 108 may also be spaced about 180 degrees apart from each other, and moreover may be radially displaced from the core apertures 104 by about 180 degrees. As a result, blood passing through the heat exchanger element 106 undergoes a spiral flow path through and around the hollow fibers within the heat exchanger element 106.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

We claim:

1. A blood processing apparatus comprising:

a housing having a blood inlet and a blood outlet, the blood inlet extending into an interior of the housing [near a first end of the housing];

a heat exchanger core arranged within the housing, the heat exchanger core configured to impart a radial flow to blood passing from the blood inlet and through a core aperture to an exterior of the heat exchanger core[, the core including one or more ribs defining indentations];

heat exchanger hollow fibers disposed about the heat exchanger core such that a heat exchanger fluid may flow through the heat exchanger hollow fibers and blood from the core aperture may flow across the heat exchanger hollow fibers;

[wherein the heat exchanger hollow fibers are supported by the one or more ribs of the heat exchanger core;]

a cylindrical shell [extending coaxially about] *surrounding* the heat exchanger [core] *hollow fibers*, the cylindrical shell including [an annular] *a* shell aperture [disposed near a second end of the housing, the shell aperture] configured to impart a longitudinal blood flow component to blood passing to an exterior of the cylindrical shell; and gas exchanger hollow fibers disposed about the cylindrical shell such that gases may flow through the gas exchange hollow fibers and blood passing from the [annular] shell aperture may flow across the gas exchanger hollow fibers;

wherein the heat exchanger core includes a blood turbulence section; and wherein the blood turbulence section comprises a recess formed within an outer surface of the heat exchanger core *downstream of the core aperture,* and a grid disposed over the recess *and under the heat exchanger hollow fibers, the core aperture being devoid of the grid*, the grid comprising a plurality of apertures extending through the grid.

2. The blood processing apparatus of claim [1] *24*, wherein the one or more ribs include one or more radially disposed core ribs configured to support the heat exchanger hollow fibers as well as provide a radial component to blood flow across the heat exchanger hollow fibers.

3. The blood processing apparatus of claim [1] *24*, wherein the one or more ribs include one or more longitudinally disposed ribs configured to support the heat exchanger hollow fibers.

4. The blood processing apparatus of claim 1, wherein the heat exchanger core includes a conical deflection surface disposed between the blood inlet and the core aperture, the conical deflection surface imparting a radial component to blood flow trajectory leaving the core aperture.

5. The blood processing apparatus of claim 1, wherein the housing includes an inner surface upon which one or more radially disposed housing ribs are disposed, the one or more radially disposed housing ribs configured to impart a radial component to blood flow trajectory across the gas exchanger hollow fibers.

6. The blood processing apparatus of claim 1, wherein the blood turbulence section comprises a plurality of longitudinally-extending indentations extending into an outer surface of the heat exchanger core.

7. The blood processing apparatus of claim 1, further comprising a first end cap secured to the housing, the blood inlet [being integrally formed] *provided* with the first end cap.

8. The blood processing apparatus of claim 7, further comprising a gas inlet [integrally formed] *provided* with the first end cap, the gas inlet in fluid communication with an interior of the gas exchanger hollow fibers.

9. The blood processing apparatus of claim 1, further comprising a second end cap secured to the housing, the second end cap including a heat exchanger fluid inlet [integrally formed] *provided* with the second end cap and a heat exchanger fluid outlet [integrally formed] *provided* with the second end cap, the heat exchanger fluid inlet and outlet each in fluid communication with an interior of the heat exchanger hollow fibers.

10. The blood processing apparatus of claim 9, further comprising a gas outlet [integrally formed] *provided* with the second end cap, the gas outlet in fluid communication with an interior of the gas exchanger hollow fibers.

11. A blood processing apparatus comprising:

a housing having a blood inlet and a blood outlet, the blood inlet extending into an interior of the housing [near a first end of the housing];

a first end cap secured to the housing, the blood inlet being integrally formed with the first end cap;

a heat exchanger core arranged within the housing, the heat exchanger core configured to impart a radial flow to blood passing from the blood inlet and through a core aperture to an exterior of the heat exchanger core[, the core including one or more ribs defining indentations];

heat exchanger hollow fibers disposed about the heat exchanger core such that a heat exchanger fluid may flow through the heat exchanger hollow fibers and blood from the core aperture may flow across the heat exchanger hollow fibers;

[wherein the heat exchanger hollow fibers are supported by the one or more ribs of the heat exchanger core;]

a cylindrical shell [extending coaxially about] *surrounding* the heat exchanger [core] *hollow fibers*, the cylindrical shell including [an annular] *a* shell aperture [disposed near a second end of the housing, the shell aperture] configured to impart a longitudinal blood flow component to blood passing to an exterior of the cylindrical shell; and gas exchanger hollow fibers disposed about the cylindrical shell such that gases may flow through the gas exchange hollow fibers and blood passing from the [annular] shell aperture may flow across the gas exchanger hollow fibers;

wherein the heat exchanger core includes a blood turbulence section that includes a recess formed within an outer surface of the heat exchanger core *downstream of the core aperture,* and a grid disposed over the recess *and under the heat exchanger hollow fibers, the core aperture being devoid of the grid*, the grid comprising a plurality of apertures extending through the grid.

12. The blood processing apparatus of claim 11, further comprising a gas inlet integrally formed with the first end cap, the gas inlet in fluid communication with an interior of the gas exchanger hollow fibers.

13. The blood processing apparatus of claim 11, further comprising a second end cap secured to the housing, the second end cap including a heat exchanger fluid inlet integrally formed with the second end cap and a heat exchanger fluid outlet integrally formed with the second end cap, the heat exchanger fluid inlet and outlet each in fluid communication with an interior of the heat exchanger hollow fibers.

14. The blood processing apparatus of claim 13, further comprising a gas outlet integrally formed with the second end cap, the gas outlet in fluid communication with an interior of the gas exchanger hollow fibers.

15. The blood processing apparatus of claim 11, wherein the cylindrical shell includes one or more shell ribs that protrude from an inner surface of the cylindrical shell and extend toward the heat exchanger core.

16. The blood processing apparatus of claim [11] *22*, wherein the one or more ribs include one or more radially disposed core ribs configured to support the heat exchanger hollow fibers as well as provide a radial component to blood flow across the heat exchanger hollow fibers.

17. The blood processing apparatus of claim [11] *22*, wherein the one or more ribs include one or more longitudinally disposed ribs configured to support the heat exchanger hollow fibers.

18. The blood processing apparatus of claim 11, wherein the heat exchanger core includes a conical deflection surface disposed between the blood inlet and the core aperture, the conical deflection surface imparting a radial component to blood flow trajectory leaving the core aperture.

19. The blood processing apparatus of claim 11, wherein the housing includes an inner surface upon which one or more radially disposed housing ribs are disposed, the one or more radially disposed housing ribs configured to impart a radial component to blood flow trajectory across the gas exchanger hollow fibers.

20. The blood processing apparatus of claim 11, wherein the blood turbulence section comprises a plurality of longitudinally-extending indentations extending into an outer surface of the heat exchanger core.

*21. The blood processing apparatus of claim 11, wherein the heat exchanger core includes one or more ribs.*

*22. The blood processing apparatus of claim 21, wherein the heat exchanger hollow fibers are supported by the one or more ribs of the heat exchanger core.*

*23. The blood processing apparatus of claim 1, wherein the heat exchanger core includes one or more ribs.*

*24. The blood processing apparatus of claim 23, wherein the heat exchanger hollow fibers are supported by the one or more ribs of the heat exchanger core.*

*25. A blood processing apparatus comprising:*

*a housing having a blood inlet extending into an interior of the housing and a blood outlet extending out of the interior of the housing;*

*a heat exchanger element arranged within the housing, the heat exchanger element including a core aperture in fluid communication with the blood inlet;*

*a cylindrical shell surrounding the heat exchanger element; and*

*a gas exchanger element surrounding the cylindrical shell;*

*wherein the heat exchanger element includes a blood turbulence section; and*

*wherein the blood turbulence section comprises a recess formed within an outer surface of the heat exchanger element downstream of the core aperture, and a grid disposed over the recess, the core aperture being devoid of the grid, the grid comprising a plurality of apertures extending through the grid;*

*wherein the heat exchanger element includes heat exchanger hollow fibers providing a heat exchanger fluid flowing through the heat exchanger hollow fibers, wherein blood may flow across the heat exchanger hollow fibers, wherein the heat exchanger hollow fibers are disposed over the grid;*

*wherein the blood processing apparatus defines a blood flow pathway from the blood inlet, across the heat exchanger element, across the gas exchanger element and to the blood outlet.*

*26. The blood processing apparatus of claim 25, wherein the heat exchanger element is configured to impart a radial flow to blood passing from the blood inlet and through the core aperture of the heat exchange element to an exterior of the heat exchanger element.*

*27. The blood processing apparatus of claim 25, wherein the cylindrical shell includes a shell aperture configured to impart a longitudinal blood flow component to blood passing to an exterior of the cylindrical shell.*

*28. The blood processing apparatus of claim 25, wherein the gas exchanger element includes gas exchanger hollow fibers disposed about the cylindrical shell providing a gas flowing through the gas exchanger hollow fibers, wherein blood may flow across the gas exchanger hollow fibers.*

*29. A blood processing apparatus comprising:*

*a housing having a blood inlet extending into an interior of the housing and a blood outlet extending out of the interior of the housing;*

*a heat exchanger element arranged within the housing, the heat exchanger element including a core aperture in fluid communication with the blood inlet;*

*a cylindrical shell surrounding the heat exchanger element; and*

*a gas exchanger element surrounding the cylindrical shell;*

*wherein the heat exchanger element includes a blood turbulence section; and*

*wherein the blood turbulence section comprises a recess formed within an outer surface of the heat exchanger element downstream of the core aperture, and a grid disposed over the recess, the core aperture being devoid of the grid, the grid comprising a plurality of apertures extending through the grid;*

*wherein the heat exchanger element includes heat exchanger hollow fibers providing a heat exchanger fluid flowing through the heat exchanger hollow fibers, wherein blood may flow across the heat exchanger hollow fibers, wherein the heat exchanger hollow fibers are disposed over the grid;*

*wherein the blood processing apparatus includes a blood flow path from the blood inlet across the blood turbulence section to the blood outlet, wherein the blood turbulence section is configured to provide turbulent blood flow across the heat exchanger element.*

* * * * *